United States Patent [19]

Martin et al.

[11] 4,250,304
[45] Feb. 10, 1981

[54] 2-DEOXY-2-SUBSTITUTED FORTIMICIN A AND B AND DERIVATIVES

[75] Inventors: Jerry R. Martin; John S. Tadanier, both of Waukegan; Paulette Johnson, Zion; Alex M. Nadzan, Gurnee, all of Ill.

[73] Assignee: Abbott Laboratories, North Chicago, Ill.

[21] Appl. No.: 79,145

[22] Filed: Sep. 26, 1979

[51] Int. Cl.³ .............................................. C07H 15/22
[52] U.S. Cl. ..................................... 536/17 R; 536/4; 424/180
[58] Field of Search ........................... 536/17 R, 17 B

[56] References Cited

U.S. PATENT DOCUMENTS 4,169,198  9/1979  Martin et al. ...................... 536/17 R
4,176,178  11/1979  Martin et al. ...................... 536/17 R Primary Examiner—Johnnie R. Brown
Attorney, Agent, or Firm—Robert L. Niblack; Gildo E. Fato; Joyce R. Niblack

[57] ABSTRACT

Disclosed are 2-deoxy-2-substituted fortimicin A and B derivatives represented by the formula

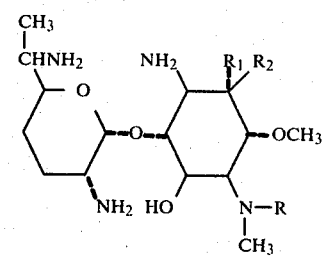

wherein R is hydrogen glycyl, β-alanyl, acetyl, or β-amino lower alkyl, $R_1$ is hydrogen, amino, azido, halo, glycylamido, β-alanyl amido or 2-O-methanesulfonyl and $R_2$ is hydrogen or halo and their pharmaceutically acceptable salts. The compounds are active antibacterial agents.

10 Claims, No Drawings

2-DEOXY-2-SUBSTITUTED FORTIMICIN A AND B AND DERIVATIVES

BACKGROUND OF THE INVENTION

Recently, a new family of aminoglycoside antibiotics, the fortimicins, have been identified. See U.S. Pat. Nos. 3,976,768 and 3,931,400 which disclose the parent antibiotics, fortimicin A and fortimicin B. Historically, once an aminoglycoside antibiotic has been in clinical use for awhile, resistant microorganisms arise. In many cases, the resistance is R-factor mediated and is attributed to the ability of the bacteria to enzymatically modify the amino or hydroxyl groups of the aminoglycoside antibiotic. It is known that in the naturally occuring fortimicin aminoglycoside antibiotics blocking the 2-hydroxy group inactivates the antibiotics. Copending applications Ser. Nos. 863,006 and 863,009 describe 2-deoxyfortimicin A and 2-deoxyfortimicin B, respectively.

SUMMARY OF THE INVENTION

2-Deoxy-2-substituted fortimicin A and B derivatives are provided by this invention as well as their salts, intermediates useful in the preparation of the compounds of this invention, processes for making the compounds, and compositions employing the antibiotics of this invention as the active component of the composition.

The compounds are administered by parenteral routes of administration in daily dosages of from about 10 to about 200 mg/kg of body weight daily.

DETAILED DESCRIPTION OF THE INVENTION

This invention provides 2-deoxy-2-substituted fortimicin A and B derivatives represented by the formula

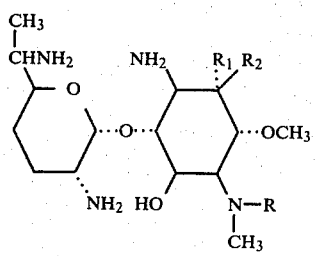

wherein R is hydrogen, glycyl, β-alanyl, acetyl or β-amino lower alkyl, $R_1$ is hydrogen, amino, azido, halo, glycylamido, β-alanylamido, or 2-O-methanesulfonyl and $R_2$ is hydrogen or halo and their pharmaceutically acceptable salts.

The term "loweralkyl" refers to straight or branched chain alkyl groups havidng from 1 to 6 carbon atoms, i.e., methyl, ethyl, n-propyl, iso-propyl, n-butyl, sec-butyl, tert-butyl, n-pentyl, n-hexyl, and the like.

The term "pharmaceutically acceptable salts" are the non-toxic acid addition salts prepared by reacting the base with a suitable organic or inorganic acid. Representative salts include the hydrochloride, hydrobromide, sulfate, bisulfate, acetate, oxylate, valerate, oleate, palmitate, stearate, laurate, borate, benzoate, lactate, phosphate, tosylate, citrate, maleate, fumarate, succinate, tartrate, napsylate and the like.

A composition-of-matter aspect of this invention includes antibacterially active 2-deoxy-2-substituted, 2-deoxy-2-epi-substituted and 2-N-alkyl-2-deoxy-2-substituted fortimicins. Of particular interest are the 2-deoxy-2-chlorofortimicins, the 2-deoxy-2-epi-chlorofortimicins, the 2-deoxy-2-aminofortimicins, the 2-deoxy-2-azidofortimicins and the 2-N-alkyl-2-deoxy-2-aminofortimicins and the non-toxic pharmaceutically acceptable acid addition salts of the foregoing which possess antibacterial activity.

Another composition-of-matter aspect of this invention relates to chemical compounds valuable as intermediates in the preparation of 2-deoxy-2-substituted fortimicins, said intermediates having a pseudodiglycoside structure. Included are 2-O-hydrocarbonsulfonyl derivatives as well as 2-O-hydrocarbonsulfonyl derivatives wherein all the primary amino groups are protected by a member selected from the group consisting of lower alkanoxy, carbobenzyloxy, lower thioalkanoxyl, thioaroyl and lower alkylthiocarbamoyl. The secondary methylamino group and neighboring group in the fortimicin B series may also be protected by an aldehyde to form an oxazolidine ring.

The processes of this invention are, in general, directed towards replacing the $C_2$ hydroxyl group of the fortamine moiety of fortimicins with a halide, azido or amino group have the natural or unnatural configuration at $C_2$ to obtain a novel fortimicin derivative having antibacterial activity. Briefly, in one process, the $C_2$ hydroxyl group of the fortimicin is converted to a $C_2$ hydrocarbon sulfonate ester which in turn is converted to an azido or epi-halide function. The azido function is readily converted to an amino group by catalytic reduction.

More specifically, by this process, fortimicin B having a $C_2$ hydroxyl function, the primary amino groups of which are protected by a member selected from the group consisting of carbobenzyloxy, lower alkanoyl, lower thioalkanoyl, thioaroyl, and lower alkylthiocarbamoyl and the $C_4$ secondary methylamino group and neighboring hydroxyl group protected by an oxazolidine ring, is reacted with a hydrocarbonsulfonyl halide or anhydride having up to 16 carbon atoms whereby is formed a 2-O-hydrocarbonsulfonylfortimicin intermediate which is then treated with mineral acid to hydrolyze the oxazolidine ring to form a 1,2',6'-tri-N-protected-2-O-hydrocarbonsulfonylfortimicin B.

In one process, the N-protecting groups of the 1,2',6'-tri-N-protected-2-O-hydrocarbonsulfonylfortimicin B are removed by conventional methods whereby is formed a 2-O-hydrocarbonsulfonylfortimicin B which rearranges under basic conditions to form a 2-deoxy-1,2-epiminofortimicin B. The 2-deoxy-1,2-epiminofortimicin B is treated with an acidic, saturated, aqueous solution of sodium azide or with hydrochloric acid in methanol/water whereby is formed a 2-azido-2-deoxyfortimicin B or 2-chloro-2-deoxyfortimicin B respectively. For conversion of the fortimicin B derivative to a fortimicin A derivative, the primary amino groups of the 2-substituted 2-deoxyfortimicin B derivative are selectively protected by converting to N-carboxybenzyloxy functions. The free $C_4$-methylamino function is acylated by the active ester or other conventional method known to those skilled in the art. Catalytic hydrogenolysis of the N-protecting groups in an acid medium forms the 2-substituted-2-deoxy-4-N-acylfortimicins B.

In an alternate process, a 4-N-acyl-per-N-protected-2-O-hydrocarbonsulfonylfortimicin is reacted with a nucleophile such as chloride or azide ion in an appropriate solvent. When the nucleophile is chloride ion a 2-epi-chloro-2-deoxy-4-N-acyl-per-N-protected-fortimicin is formed. When the nucleophile is azide a 2-azido-2-deoxy-4-N-acyl-per-N-protected fortimicin is isolated. The N-blocking groups of the resulting 2-deoxy-2-substituted-4-N-acyl-per-N-protected fortimicins are removed by convenient methods, preferably in an acidic medium, to give the 2-deoxy-2-substituted-4-N-acyl-per-N-protected-fortimicins.

The 2-deoxy-2-chloro- or 2-deoxy-2-azido-4-N-acyl-fortimicins are also conveniently prepared from the appropriate 2-deoxy-1,2-epimino-4-N-acylfortimicins by treatment with hydrochloric acid in methanol/water or with an acidic, saturated, aqueous solution of sodium azide whereby is formed a 2-chloro-2-deoxy-4-N-acyl-fortimicin or a 2-azido-2-deoxy-4-N-acylfortimicin respectively. The 2-deoxy-1, 2-epimino-4-acylfortimicin is prepared by catalytically removing the N-blocking groups of a per N-protected 2-O-hydrocarbonsulfonyl-4-N-acylfortimicin and allowing the N-deblocked fortimicin derivative to stand at basic pH whereby is generated the 1,2-epimino function.

The 2-deoxy-2-amino-2,4-di-N-acylfortimicins are conveniently prepared by selective reduction of the 2-azido function of the 2-azido-2-deoxy-4-N-acyl-per-N-protected fortimicin to an amino grouping. The latter reduction is conveniently performed catalytically with platinum on carbon. The 2-amino function is then acylated by conventional methods and the N-protecting groups are removed in acidic medium as before.

The compounds of this invention are active as systemic antibiotics when injected by parenteral routes of administration, i.e., by the intramuscular, intravenous, intraperitoneal or subcutaneous routes of administration. The compounds can also be administered orally in those instances where it is desirable to sterilize the intestinal tract and can additionally be applied topically or rectally.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspension, syrups and elixirs containing inert diluents commonly used in the art, such as water. Besides, such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions suspension, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized, by for example, filtration through a bacteria-retaining filter, by incorporating sterilizing agents into the compositions. They can also be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 10 to 200 mg/kg of body weight daily are administered to a mammalian patient suffering from an infection caused by susceptible organism.

2-Substituted-2-deoxy-4-N-alkylfortimicin B derivatives are conveniently prepared by treating a per-N-protected-2-substituted-2-deoxy-4-N-acylfortimicin, prepared as the foregoing, with a boron hydride reducing agent followed by subsequent removal of the N-protecting groups.

The following examples further illustrate the present invention.

EXAMPLE 1

1,2',6'-Tri-N-benzyloxycarbonylfortimicin b (1)

To a stirred solution of 2.0 g of fortimicin B, 30 ml of water and 60 ml of methanol, cooled in an ice bath, is added 4.44 g of N-(benzyloxycarbonyloxy)succinimide. Stirring is continued at 0° for 3 hours and then at room temperature for 22 hours. The major portion of the methanol is evaporated under reduced pressure and the residue is shaken with a mixture of chloroform and water. The chloroform solution is washed with water and dried over anhydrous magnesium sulfate. The chloroform is evaporated and the residue is chromatographed on silica gel. Elution with a solvent system composed of chloroform-methanol-concentrated ammonium hydroxide (23.4:1.4:0.1 v/v/v) gives 1.05 g of 1,2',6'-tri-N-benzyloxycarbonylfortimicin B: $[\alpha]_D^{25}$ +16.5° (c 1.0, $CH_3OH$); IR ($CDCl_3$) 1712 and 1507 $cm^{-1}$; NMR ($CDCl_3$) $\delta 1.03$ ($C_{6'}$—$CH_3$, $J_{6',7'}=6.0$ Hz), 2.32 ($C_4$—$NCH_3$), 3.41 ($C_3$—$OCH_3$).

Anal. Calcd. for $C_{39}H_{50}N_4O_{11}$: C, 62.39; H, 6.71; N, 7.46. Found: C, 62.16; H, 6.76; N, 7.43.

EXAMPLE 2

1,2',6'-Tri-N-benzyloxycarbonyl-4,5-salicylaldehyde oxazolidine fortimicin B (2)

A solution of 22 g of 1,2',6'-tri-N-benzyloxycarbonyl-fortimicin B in 396 ml of methanol is treated with 3.96 ml of salicylaldehyde and refluxed for 1 hour. Evaporation of the reaction mixture under reduced pressure gives 26 g of 1,2',6'-tri-N-benzyloxycarbonyl-4,5-salicylaldehyde oxazolidine fortimicin B as a brownish yellow solid: NMR ($CDCl_3$) $\delta 0.94$ ($C_{6'}$—$CH_3$, $J_{6',7'}=7.0$ Hz), 2.34 ($C_4$—$NCH_3$), 3.49 ($C_3$—$OCH_3$), 7.31 (Cbz-aromatic).

EXAMPLE 3

1,2',6'-Tri-N-benzyloxycarbonyl-4,5-(2-O-methanesulfonylsalicylaldehyde) oxazolidine-2-O-methanesulfonylfortimicin B (3)

A stirred solution of 26 g of 1,2',6'-tri-N-benzyloxycarbonyl-4,5-salicylaldehyde oxazolidine fortimicin B in 154 ml of dry pyridine is treated with 12.26 ml of freshly distilled methane sulfonyl chloride. After stirring for 20 hours the reaction mixture is poured into 2000 ml of 5% sodium hydrogen carbonate solution and extracted 2 times with 1000 ml portions of chloroform. The combined chloroform extract is washed with 1000 ml of 5% sodium hydrogen carbonate and then twice with 1000 ml portions of water. The chloroform is evaporated under reduced pressure and the pyridine is removed by repeated co-distillation with benzene to give 31.2 g of 1,2',6'-tri-N-benzyloxycarbonyl-4,5-(2-O-methanesulfonylsalicylaldehyde) oxazolidine-2-O-methanesulfonylfortimicin B: NMR (CDCl$_3$) $\delta$1.0 (C$_{6'}$—CH$_3$, J$_{6',7'}$=7.0 Hz), 2.19 (C$_4$—NCH$_3$), 2.94 (C$_2$—OSO$_2$CH$_3$), 3.15 (Ar—OSO$_2$CH$_3$), 3.60 (C$_3$—OCH$_3$), 7.33 (Cbz-aromatic).

EXAMPLE 4

1,2',6'-Tri-N-benzyloxycarbonyl-2-O-methanesulfonylfortimicin b (4)

A stirred solution of 31.2 g of 1,2',6'-tri-N-benzyloxycarbonyl-4,5-(2-O-methanesulfonylsalicylaldehyde) oxazolidine-2-O-methanesulfonylfortimicin B in 1000 ml of tetrahydrofuran is treated with 262 ml of 0.4 N hydrochloric acid. After stirring for 4 hours, the reaction mixture is poured into 5700 ml of 6 N ammonium hydroxide solution and extracted 2 times with 1400 ml portions of chloroform. The combined chloroform extract is washed with 5700 ml of 7% sodium hydrogen sulfite solution and then 2 times with 1180 ml portions of water. Removal of the chloroform under reduced pressure gives 27.35 g of crude 1,2',6'-tri-N-benzyloxycarbonyl-2-O-methanesulfonylfortimicin B. The crude material is chromatographed on a column (6.0×80 cm) of Sephadex LH-20 gel prepared and eluted with 95% ethanol. Fractions containing the desired material are combined and concentrated to dryness under reduced pressure to give pure 1,2',6'-tri-N-benzyloxycarbonyl-2-O-methanesulfonylfortimicin B as a glass: $[\alpha]_D^{23}+18.5°$ (c 1.0, CH$_3$OH); IR (CDCl$_3$) 3436, 3350, 1703, 1502, 1354 and 1173 cm$^{-1}$; NMR (CDCl$_3$) $\delta$1.07 (C$_{6'}$—CH$_3$, J$_{6',7'}$=7.0 Hz), 2.34 (C$_4$—NCH$_3$), 2.87 (OSO$_2$CH$_3$), 3.48 (C$_3$—OCH$_3$).

Anal. Calcd. for C$_{40}$H$_{52}$N$_4$O$_{13}$S:C, 57.96; H, 6.32; N, 6.76. Found: C, 57.65; H, 6.52; N, 6.62.

EXAMPLE 5

Tetra-N-benzyloxycarbonyl-2-O-methanesulfonylfortimicin A (5)

A stirred solution of 2.267 g of 1,2',6'-tri-N-benzyloxycarbonyl-2-O-methanesulfonylfortimicin B in 14 ml of dry tetrahydrofuran is treated for 20 hours with 1.005 g of the N-hydroxysuccinimide ester of N-benzyloxycarbonylglycine. The tetrahydrofuran is evaporated under reduced pressure to give a lemon-yellow solid. The solid is chromatographed on a column (3.0×74 cm) of silica gel prepared and eluted with a solvent system consisting of benzene-methanol-95% ethanol-concentrated ammonium hydroxide (23.5:1.4:2.0:0.2 v/v). Elutes containing only the major product are evaporated to dryness to give 1.789 g of tetra-N-benzyloxycarbonyl-2-O-methanesulfonylfortimicin A: $[\alpha]_D^{24}+40.7°$ (c 1.0, methanol); IR (CDCl$_3$) 3427, 1710, 1635 and 1495 cm$^{-1}$; NMR (CDCl$_3$) $\delta$1.15 (d, C$_{6'}$—CH$_3$, J$_{6',7'}$=7.0 Hz), 2.81 (s, C$_4$—NCH$_3$), 3.02 (s, C$_2$—OSO$_2$CH$_3$), 3.50 (s, C$_3$—OCH$_3$), 7.25 (m, Cbz-aromatic).

Anal. Calcd. for C$_{50}$H$_{61}$N$_5$O$_{16}$S:C, 58.87, H, 6.03; N, 6.87; S, 3.14 Found: C, 58.70; H, 6.04; N, 6.62; S. 2.89.

EXAMPLE 6

2-O-Methanesulfonylfortimicin A Tetrahydrochloride (6)

A solution prepared from 5.0 g of 1,2',6',2"-tetra-N-benzyloxycarbonyl-2-O-methanesulfonylfortimicin A and 425 ml of 0.2 N hydrochloric acid in methanol is hydrogenolyzed for 4 hours under 3 atmospheres of hydrogen in the presence of 5.0 g of 5% palladium on carbon. The catalyst is removed by filtration and the methanol is evaporated under reduced pressure. Residual water and excess acid is removed by repeated co-distillation with methanol under reduced pressure to yield 2.753 g of 2-O-methanesulfonylfortimicin B tetrahydrochloride; $[\alpha]_D^{25}+79.8°$ (c 1.0, methanol); IR (KBr) 3420, 2930, 1640, 1590, 1485, 1332 and 1143 cm$^{-1}$; NMR (D$_2$O external TMS) $\delta$1.81 (d, C$_{6'}$—CH$_3$, J$_{6',7'}$=7.0 Hz), 3.61 (s, C$_4$—NCH$_3$), 3.83 (s, C$_2$—O-SO$_2$CH$_3$), 4.07 (s, C$_3$—OCH$_3$), 5.81 (d, H$_{1'}$, J$_{1',2'}$=3.0 Hz); mass spec. (M+.—SO$_2$CH$_2$) m/e 405.

EXAMPLE 7

2-Deoxy-1,2-epiminofortimicin A (7)

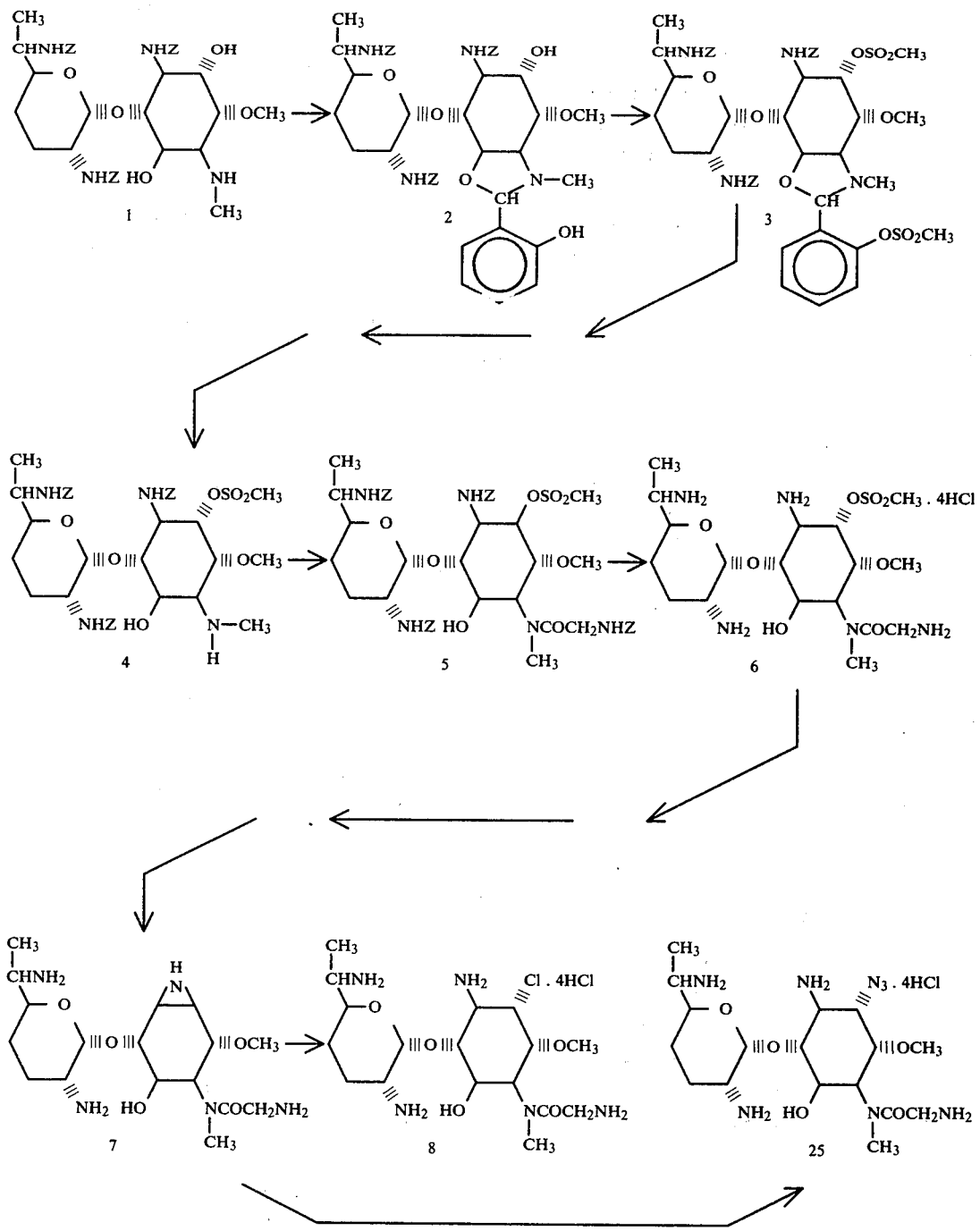

A solution prepared from 1.40 g of 2-O-methanesulfonylfortimicin A tetrahydrochloride in 15 ml of water is passed through a column of an anion exchange resin, quarternary ammonium styrene type, e.g. AG2 X8, 50–100 mesh, hydroxyl form, sold by Bio-Rad Laboratories, sufficient to remove the chloride ion. Basic elutes are combined and allowed to stand at room temperature for 120 hours. After evaporation of a major portion of the water the solution is again passed through a column of an anion exchange resin, of the type described above, sufficient to removed the methanesulfonic acid generated on formation of the 1,2-epimino ring. Basic elutes are combined and taken to dryness under reduced pressure to give 1.121 g of 2-deoxy-1,2-epiminofortimicin A:

NMR ($D_2O$ external TMS) $\delta 1.12$ ($C_{6'}$—$CH_3$, $J_{6',7'} = 7.0$ Hz); 3.51 (s, $C_4$—$NCH_3$), 3.96 (s, $C_3$—$OCH_3$), 5.41 (d, $H_{1'}$, $J_{1',2'} = 3.0$ Hz).

EXAMPLE 8

2-Chloro-2-deoxyfortimicin A Tetrahydrochloride (8)

A solution prepared from 0.5 g of 2-deoxy-1,2-epiminofortimicin A and 100 ml of 0.2 N hydrochloric acid in methanol is allowed to stand 0.5 hours. The methanol is evaporated under reduced pressure. Residual water and excess acid is removed by co-distillation with methanol under reduced pressure to give 2-chloro-2-deoxyfortimicin A tetrahydrochloride: IR (KBr) 3420, 1640, 1595 and 1490 cm$^{-1}$; NMR (D$_2$O external TMS) δ1.82 (d, C$_{6'}$—CH$_3$, J$_{6',7'}$=7.0 Hz), 3.61 (s, C$_4$—NCH$_3$), 3.98 (s, C$_3$—OCH$_3$), 5.80 (d, H$_{1'}$, J$_{1',2'}$=3.0 Hz).

EXAMPLE 9

2-Azido-2-deoxyfortimicin A Tetrahydrochloride (25)

A solution prepared from 1.160 g of 1,2-epiminofortimicin A and 72 ml of a saturated solution of aqueous sodium azide is adjusted to pH 5.0 with hydrochloric acid. After standing at room temperature for 60 hours the solution is concentrated to dryness under reduced pressure. The residue is passed through a column (2.2×100 cm) of Sephadex G-15 (sold by Pharmacia Fine Chemicals, Inc) prepared and eluted with 0.1 N acetic acid. Elutes containing the major component are collected and taken to dryness to leave 0.446 g of residue. The residue is rapidly chromatographed on a column (1.8×41 cm) of silica gel prepared and eluted with a solvent system consisting of the lower phase of a mixture of chloroform-methanol-concentrated ammonium hydroxide (1:1:1 v/v/v). Fractions containing only the major component are taken to dryness and the residue is dissolved in 50 ml of 0.2 N hydrochloric acid in methanol. The solution is evaporated to dryness and excess hydrochloric acid is removed by repeated co-distillation with methanol to give 0.381 g of 2-azido-2-deoxyfortimicin A tetrahydrochloride: IR (KBr) 3425, 2920, 2105, 1630, 1585 and 1428 cm$^{-1}$; NMR (D$_2$O) δ1.83 (d, C$_{6'}$—CH$_3$, J$_{6',7'}$=7.0 Hz), 3.60 (s, C$_4$—NCH$_3$), 4.04 (s, C$_3$—OCH$_3$), 5.79 (d, H$_{1'}$, J$_{1',2'}$=3.5 Hz).

EXAMPLE 10

2-O-Methanesulfonylfortimicin B Tetrahydrochloride (9)

A solution of 4.42 g of 1,2',6'-tri-N-benzyloxycarbonyl-2-O-methanesulfonylfortimicin B in 310 ml of 0.2 N hydrochloric acid in methanol is treated for 4 hours with 4.5 g of 5% palladium on carbon under 3 atmospheres of hydrogen. The catalyst is filtered off and washed with ethanol. The filtrate is concentrated to dryness under reduced pressure and the excess hydrochloric acid is removed by repeated co-distillation with methanol to leave 2.79 g of 2-O-methanesulfonylfortimicin B tetrahydrochloride as a white glass: [α]$_D^{25}$+91.7° (c 1.01, CH$_3$OH); IR (KBr) 3400, 2920, 1590, 1330 and 1165 cm$^{-1}$; NMR (D$_2$O external TMS) δ1.82 (C$_{6'}$—CH$_3$, J$_{6',7'}$=7.0 Hz), 3.31 (C$_4$—NCH$_3$), 3.88 (C$_2$—OS$_2$CH$_3$), 4.07 (C$_3$—OCH$_3$), 5.88 (H$_{1'}$ J$_{1',2'}$=4.0 Hz).

EXAMPLE 11

1,2-Epiminofortimicin B (10)

A solution prepared from 2.8 g of 2-O-methanesulfonyl fortimicin B tetrahydrochloride in 20 ml of water is passed through a column (2.2×20 cm) of an anion exchange resin, quarternary ammonium styrene type, e.g., AG ® 2-X8, 50–100 mesh resin, (OH$^-$ form) sold by Bio-Rad Laboratories, sufficient to remove the chloride ion. Basic elutes are combined and allowed to stand at room temperature for 72 hours. Evaporation of the water under reduced pressure leaves 3.0 g of 1,2-epiminofortimicin B: NMR (D$_2$O external TMS) δ1.55 (C$_{6'}$—CH$_3$, J$_{6',7'}$=7.0 Hz), 2.83 (C$_4$—NCH$_3$), 4.02 (C$_3$—OCH$_3$), 5.42 (H$_{1'}$, J$_{1',2'}$=3.0 Hz).

EXAMPLE 12

2-Chloro-2-deoxyfortimicin B Tetrahydrochloride (11)

A solution prepared from 2.90 g of 1,2-epiminofortimicin B in 200 ml of 0.2 N hydrochloric acid in methanol is allowed to stand at room temperature for 5.5 hours. The reaction mixture is concentrated to dryness under reduced pressure and excess hydrochloric acid is removed by repeated co-distillation with methanol to leave 3.935 g of 2-chloro-2-deoxyfortimicin B tetrahydrochloride: IR (KBr) 3400, 2940, 1590, and 1505 cm$^{-1}$; mass spectrum, m/e 366.2057, calcd. for C$_{15}$H$_{31}$ClN$_4$O$_4$, 366.2033.

EXAMPLE 13

2-Chloro-2-deoxyfortimicin B (12)

A solution prepared from 2.2 g of 2-chloro-2-deoxyfortimicin B tetrahydrochloride in 10 ml of water is applied to a column (2.2×11 cm) of an anion exchange resin, quarternary ammonium styrene type, e.g., AG ® 2-X8, 50–100 mesh resin, hydroxyl form, sold by Bio-Rad Laboratories. After elution with water the basic elutes are concentrated to dryness under reduced pressure to give 2.1 g of 2-chloro-2-deoxyfortimicin B: NMR (D$_2$O external TMS) δ1.51 (d, C$_{6'}$—CH$_3$, J$_{1',2'}$=7.0 Hz), 2.88 (s, C$_4$—NCH$_3$), 4.00 (s, C$_3$—OCH$_3$), 5.52 (d, H$_{1'}$, J$_{1',2'}$=4.0 Hz).

EXAMPLE 14

1,2',6'-Tri-N-benzyloxycarbonyl-2-chloro-2-deoxyfortimicin B (13)

A stirred, ice-bath cooled solution prepared from 2.1 g of 2-chloro-2-deoxyfortimicin B, 23 ml of water and 46 ml of methanol is treated with 3.45 g of N-(benzyloxycarbonyloxy)succinimide. Stirring is continued at 0° for 3 hours and then at room temperature for 14 hours. The major portion of the methanol is evaporated under reduced pressure and the residue is shaken with a mixture of 125 ml of water and 75 ml of chloroform. The chloroform is separated and the aqueous portion is again shaken with 75 ml of chloroform. The combined chloroform extract is dried over anhydrous magnesium sulfate. After evaporation of the chloroform the residue is chromatographed on a column of silica gel. Elution with a solvent system consisting of benzene-methanol-95% ethanol-concentrated ammonium hydroxide (23.5:1.4:2.0:0.2 v/v) gives 1.237 g of 1,2',6'-tri-N-benzyloxycarbonyl-2-chloro-2-deoxyfortimicin B: NMR (CDCl$_3$) δ1.07 (d, C$_{6'}$—CH$_3$, J$_{6',7'}$=6.5 Hz), 2.31 (s, C$_4$—NCH$_3$), 3.43 (s, C$_3$—OCH$_3$), 4.92 (d, H$_{1'}$, J$_{1',2'}$=4.0 Hz), 7.33 (m, Cbz-aromatic).

EXAMPLE 15

Tetra-N-benzyloxycarbonyl-2-chloro-2-deoxyfortimicin A (14)

A stirred solution prepared from 0.635 g of 1,2',6'-tri-N-benzyloxycarbonyl-2-chloro-2-deoxyfortimicin B and 11 ml of dry tetrahydrofuran is treated with 0.328 g of the N-hydroxysuccinimide ester of N-benzyloxycarbonylglycine. After stirring at room temperature for 18 hours the tetrahydrofuran is evaporated under reduced pressure to give a residue which is applied to a column (2.0×65 cm) of silica gel and eluted with a solvent system consisting of benzene-methanol-95% ethanol-concentrated ammonium hydroxide (23.5:1.4:2.0:0.2 v/v). Elutes containing only the major product are evaporated to dryness to give 0.610 g of tetra-N-benzyloxycarbonyl-2-chloro-2-deoxyfortimicin A.

EXAMPLE 16

2-Chloro-2-deoxyfortimicin A Tetrahydrochloride (8)

A solution prepared from 0.610 g of tetra-N-benzyloxycarbonyl-2-chloro-2-deoxyfortimicin A in 75 ml of 0.2 N hydrochloric acid in methanol is treated for 4 hours with 0.61 g of 5% palladium on carbon under 3 atmospheres of hydrogen. The catalyst is collected on a filter and washed with methanol. The filtrate is evaporated to dryness under reduced pressure and excess hydrochloric acid is removed by repeated co-distillation with methanol to leave 0.384 g of 2-chloro-2-deoxyfortimicin A tetrahydrochloride: IR (KBr) 3420, 1640, 1595 and 1490 cm$^{-1}$; NMR (D$_2$O external TMS) $\delta$1.82 (d, C$_{6'}$—CH$_3$, J$_{6',7'}$=7.0 Hz), 3.61 (s, C$_4$—NCH$_3$), 3.98 (s, C$_3$—OCH$_3$), 5.80 (d, H$_{1'}$, J$_{1',2'}$=3.0 Hz).

EXAMPLE 17

1,2',6'-Tri-N-benzyloxycarbonyl-2-deoxy-2,4-epiminofortimicin B over anhydrous magnesium sulfate. The chloroform is evaporated under reduced pressure and the dimethylformamide is removed by repeated co-distillation with toluene. The residue is chromatographed on a column of silica gel using a solvent-system composed of ethyl acetate-95% ethanol-concentrated ammonium hydroxide (9.5:0.5:0.05 v/v). The first fractions eluted are discarded. Later fractions are combined and evaporated to dryness to leave as a major component 0.381 g of 1,2',6'-tri-N-benzyloxycarbonyl-2-deoxy-2,4-epiminofortimicin B [$\alpha$]$_D^{23}$+40.6° (c 1.0, methanol); IR (CDCl$_3$) 3439, 1710 and 1500 cm$^{-1}$; NMR (CDCl$_3$) $\delta$1.05 (d, C$_{6'}$—CH$_3$, J$_{6',7'}$=6.0 Hz) 2.54 (s, C$_4$—NCH$_3$), 3.23 (s, C$_3$—OCH$_3$), 7.31 (m, Cbz-aromatic).

Anal. Calcd. for C$_{39}$H$_{48}$N$_4$O$_{10}$: C, 63.92; H, 6.60; N, 7.65. Found: C, 63.91; H, 6.55; N, 7.90.

EXAMPLE 18

2-O-Methanesulfonylfortimicin A Tetrahydrochloride (6)

A solution of 2.236 g of tetra-N-benzyloxycarbonyl-2-O-methanesulfonylfortimicin A in 200 ml of 0.2 N hydrochloric acid in methanol is hydrogenolyzed over 2.20 g of 5% palladium on carbon for 4 hours. The

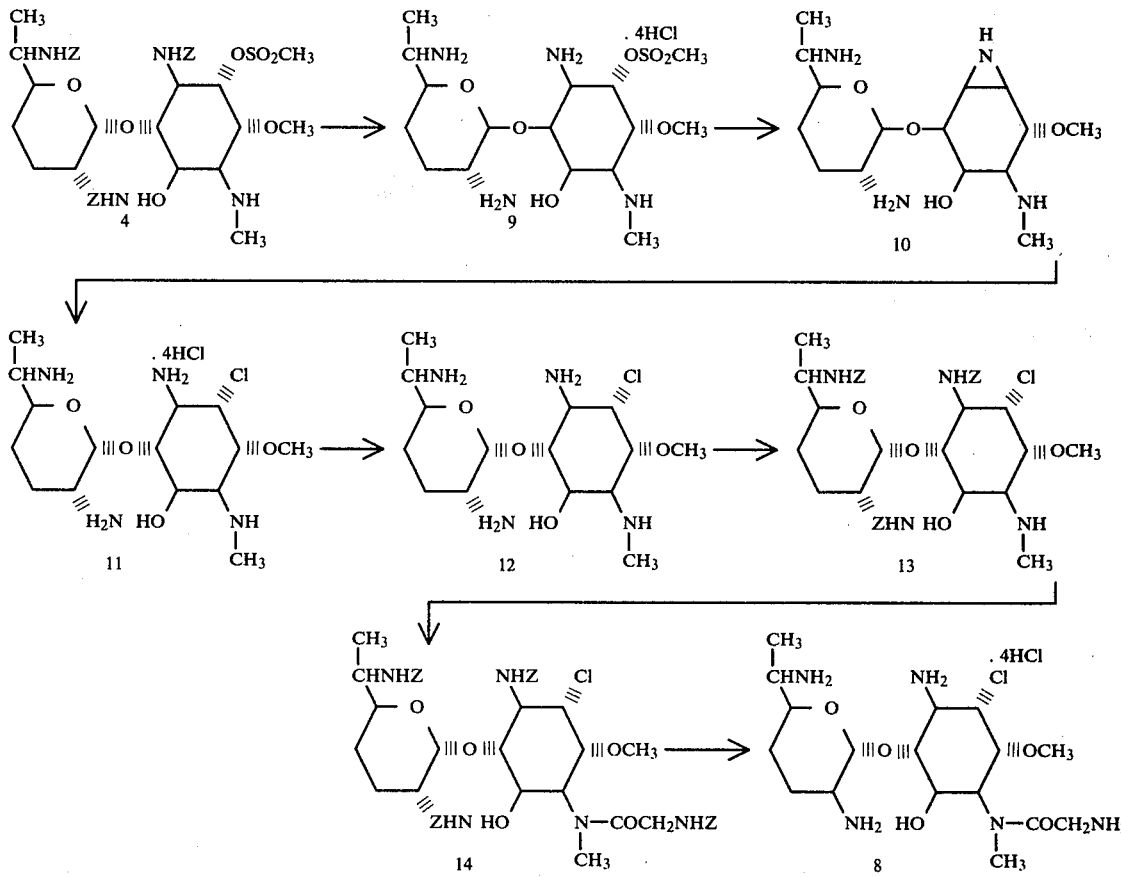

To a stirred solution of 2.0 g of 1,2',6'-tri-N-benzyloxycarbonyl-2-O-methanesulfonylfortimicin B in 111 ml of dry dimethylformamide, heated to 93° in an oil bath, is added 2.0 g of powdered sodium azide. Stirring is continued at 93° for 18 hours. After cooling to room temperature the reaction mixture is poured into 1100 ml of water and extracted three times with 360 ml portions of chloroform. The combined chloroform extract is washed twice with 360 ml portions of water and dried catalyst is collected on a filter and washed with methanol. The filtrate is concentrated to dryness and the excess hydrochloric acid is removed by repeated co-distillation with methanol under reduced pressure to give 1.40 g of 2-O-methanesulfonylfortimicin A tetrahydrochloride: [$\alpha$]$_D^{25}$+79.8° (c 1.0, methanol); IR (KBr) 3420, 2930, 1640, 1590, 1485, 1332, and 1143 cm$^{-1}$;

NMR (D$_2$O external TMS) δ1.81 (d, C$_{6'}$—CH$_3$, J$_{6',7'}$=7.0 Hz), 3.61 (s, C$_4$—NCH$_3$), 3.83 (s, C$_2$—O-SO$_2$CH$_3$) 4.07 (S, C$_3$—OCH$_3$), 5.82 (d, H$_{1'}$, J$_{1',2'}$=3.0 Hz).

EXAMPLE 19

2-Amino-2-deoxyfortimicin A (19)

A solution prepared from 0.174 g of 2-azido-2-deoxyfortimicin A and 40 ml of 0.2 N hydrochloric acid in methanol is hydrogenated over 0.20 g of palladium on carbon for 4 hours. The catalyst is collected on a filter and washed with methanol. The filtrate is concentrated to dryness and the excess hydrochloric acid is removed by repeated codistillation with methanol under reduced pressure to give 0.157 g of 2-amino-2-deoxyfortimicin A as the pentahydrochloride: [α]$_D^{25}$+80.1° (c 1.03, methanol); IR (KBr) 3410, 2940, 1645, 1590 and 1486 cm$^{-1}$; mass spectrum m/e 404.2744 (M+), Calcd. for C$_{17}$H$_{36}$N$_6$O$_5$ 404.2747.

EXAMPLE 20

2-Azido-1,2',6'-tri-N-benzyloxycarbonyl-2-deoxyfortimicin B (17)

A stirred, ice-bath cooled solution prepared from 2.0 g of 2-azido-2-deoxyfortimicin B, 20 ml of water and 40 ml of methanol is treated with 3.30 g of N-(benzyloxycarbonyloxy)succinimide. Stirring is continued in the cold for 3 hours and then at room temperature for 16 hours. The major portion of the methanol is evaporated under reduced pressure and the residue is shaken with a mixture of 60 ml of chloroform and 125 ml of water.

EXAMPLE 21

2-Azido-2-deoxyfortimicin B (16)

A solution prepared from 2.035 g of 2-deoxy-1,2-epiminofortimicin B and 120 ml of an aqueous saturated solution of sodium azide is adjusted to pH 5.0 with hydrochloric acid and allowed to stand at room temperature for 48 hours. The water is removed under reduced pressure and the residue is chromatographed on a column (1.8×51 cm) of silica gel prepared and eluted with a solvent system consisting of the lower phase of a mixture of chloroform-methanol-concentrated ammonium hydroxide (1:1:1 v/v). The elutes are concentrated to dryness to give 1.71 g of residue. The residue is chromatographed on a column (2.0×41 cm) of cation exchange resin, e.g. Bio-Rad Laboratories, Bio-Rex ® 70, 100–200 mesh, NH+ form, and eluted with a gradient of water to 1 N ammonium hydroxide. Fractions containing the major compound are taken to dryness to give a residue which is dissolved in 0.2 N hydrochloric acid in methanol. The methanol is evaporated and the excess hydrochloric acid is removed by repeated co-distillation with methanol under reduced pressure to give 2-azido-2-deoxyfortimicin B isolated as the tetrahydrochloride: IR (KBr) 2100, 1583 and 1490 cm$^{-1}$; NMR (D$_2$O external TMS) δ1.84 (d, C$_{6'}$CH$_3$, J$_{6',7'}$=6.5 Hz), 3.32 (s, C$_4$—NCH$_3$), 4.07 (s, C$_3$—OCH$_3$), 5.89 (d, H$_{1'}$, J$_{1',2'}$=3.5 Hz).

EXAMPLE 22

2-Amino-2-deoxy-2-N-glycylfortimicin A

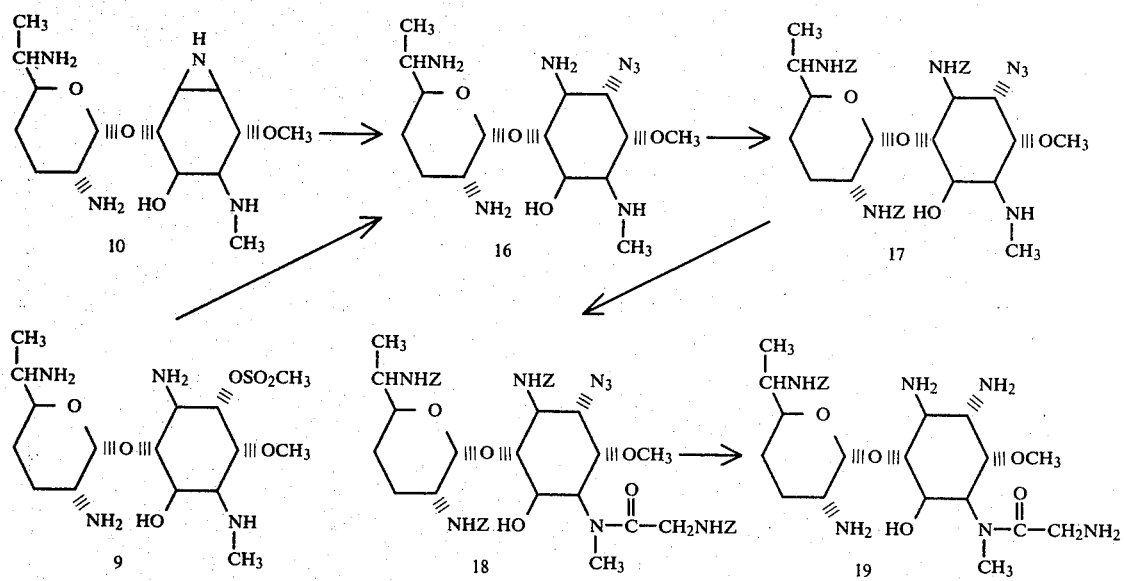

Pentahydrochloride (24)

A solution prepared from 0.081 g of 2-amino-penta-N-benzyloxycarbonyl-2-deoxy-2-N-glycylfortimicin A, 10 ml of 0.2 N hydrochloric acid in methanol and 20 ml of methanol is treated for 4 hours with 0.080 g of 5% palladium on carbon under 3 atmospheres of hydrogen. The catalyst is collected on a filter and washed with several small portions of methanol. The filtrate is evaporated to dryness under reduced pressure to give a white solid. Excess hydrochloric acid is removed by repeated co-distillation with methanol to leave 0.045 g of 2-amino-2-deoxy-2-N-glycylfortimicin A pentahy- The aqueous portion is extracted with an additional 60 ml of chloroform. The combined chloroform extract is dried over anhydrous magnesium sulfate and evaporated. The residue is chromatographed on a column of silica gel. Elution with a solvent system consisting of benzene-methanol-95% ethanol-concentrated ammonium hydroxide (23.5:1.4:2.0:0.2 v/v) gives 2-azido-1,2',6'-tri-N-benzyloxycarbonyl-2-deoxyfortimicin B identical with the material prepared in Example 17.

drochloride: $[\alpha]_D^{24} +54°$ (c 1.0, methanol); IR (KBr) 3410, 2930, 1680, 1640, 1570 and 1480 cm$^{-1}$; NMR (D$_2$O external TMS) $\delta$1.78 (d, C$_6'$CH$_3$, J$_{6',7'}$=7.0 Hz), 3.57 (s, C$_4$—NCH$_3$), 3.87 (s, C$_3$—OCH$_3$), 5.80 (d, H$_{1'}$, J$_{1',2'}$=3.0 Hz); mass spectrum, m/e 461.2936, calcd. for C$_{19}$H$_{39}$N$_7$O$_6$, 461.2962.

EXAMPLE 23

2-Amino-penta-N-benzyloxycarbonyl-2-deoxy-2-N-glycylfortimicin A (23)

A stirred solution of 0.171 g of 2-amino-1,2′,6′,2″-tetra-N-benzyloxycarbonyl-2-deoxyfortimicin A in 3.0 ml of dry tetrahydrofuran is treated for 18 hours with 0.067 g of the N-hydroxysuccinimide ester of N-benzyloxycarbonylglycine. The tetrahydrofuran is evaporated under reduced pressure to leave a white residue which is chromatographed on a column (1.3×57 cm) of silica gel prepared and eluted with a solvent system consisting of benzene-methanol-95% ethanol-concentrated ammonium hydroxide (23.4:1.4:2.0:0.2 v/v). Fractions containing the major product are taken to dryness and the residue is rechromatographed on the same system described above. Eluates containing only the major product are evaporated to leave 0.177 g of 2-amino-penta-N-benzyloxycarbonyl-2-deoxy-2-N-glycylfortimicin A: $[\alpha]_D^{24}+39°$ (c 1.0, methanol); IR (CDCl$_3$) 3405, 3350, 1700, 1633 and 1497 cm$^{-1}$; NMR (CDCl$_3$) $\delta$1.13 (C$_6'$—CH$_3$, J$_{6',7'}$=7.0 Hz), 2.70 (s, C$_4$—NCH$_3$), 3.26 (s, C$_3$—OCH$_3$), 7.34 (m, Cbz-aromatic).

Anal. Calcd. for C$_{59}$H$_{69}$N$_7$O$_{16}$: C, 62.59; H, 6.14; N, 8.66. Found: C, 62.19; H, 6.15; N, 8.42.

EXAMPLE 24

2-Deoxy-2-epi-chlorofortimicin A Tetrahydrochloride (2)

A solution of 0.192 g of tetra-N-benzyloxycarbonyl-2-deoxy-2-epi-chlorofortimicin A in 20 ml of 0.2 N hydrochloric acid in methanol is treated for 4 hours with 0.20 g of 5% palladium on carbon under 3 atmospheres of hydrogen. The catalyst is collected on a filter and washed with methanol. The filtrate is evaporated to dryness under reduced pressure and excess hydrochloric acid is removed by repeated co-distillation with methanol to leave 0.116 g of 2-deoxy-2-epi-chlorofortimicin A isolated as the tetrahydrochloride: $[\alpha]_D^{24}+51°$ (c 1.02, CH$_3$OH); IR (KBr) 3410, 2950, 1635, 1585, and 1480 cm$^{-1}$; NMR (D$_2$O external TMS) $\delta$1.86 (d, C$_6'$—CH$_3$, J$_{6',7'}$=7.5 Hz), 3.70 (s, C$_4$—NCH$_3$), 4.12 (s, C$_3$—OCH$_3$), 5.89 (d, H$_{1'}$, J$_{1',2'}$=4.0 Hz); mass spectrum, (M+.) 423.2229, calcd. for C$_{17}$H$_{34}$ClN$_5$O$_5$, 423.2249.

EXAMPLE 25

Tetra-N-benzyloxycarbonyl-2-deoxy-2-epi-chlorofortimicin A (20)

A stirred solution, prepared from 3.093 g of tetra-N-benzyloxycarbonyl-2-O-methanesulfonylfortimicin A and 162 ml of dry dimethylformamide is heated to 93° and treated with 3.092 g of finely powdered lithium chloride. After stirring for 52 hours at 93° and then at room temperature for 20 hours the reaction mixture is poured into 1620 ml of water and extracted three times with 540 ml portions of chloroform. The combined chloroform extracts are washed twice with 540 ml portions of water and dried over anhydrous magnesium sulfate. The chloroform is evaporated under reduced pressure and the dimethylformamide is removed by repeated codistillation with toluene to leave 2.713 g of residue. The residue is chromatographed on a column (2.1×75 cm) of silica gel using a solvent system composed of benzene-methanol-95% ethanol-concentrated ammonium hydroxide (23.5:1.4:2.0:0.2 v/v). Eluates containing only the major product are evaporated to leave 0.869 g of tetra-N-benzyloxycarbonyl-2-deoxy-2-epi-chlorofortimicin A: $[\alpha]_D^{24}+37°$ (c 1.04, methanol); IR (CDCl$_3$) 3440, 1710, 1638 and 1503 cm$^{-1}$; NMR (CDCl$_3$) $\delta$1.17 (d, C$_6'$—CH$_3$, J$_{6',7'}$=7.0 Hz), 2.85 (s, C$_4$—NCH$_3$), 3.46 (s, C$_3$—OCH$_3$) 7.31 (m, Cbz-aromatic).

Anal. Calcd. for C$_{49}$H$_{58}$N$_5$O$_{13}$Cl: C, 61.28; H, 6.09; N, 7.29; Cl, 3.69. Found: C, 61.36; H, 6.21; N, 7.00; Cl, 3.97.

EXAMPLE 26

2-Amino-1,2′,6′,2″-tetra-N-benzyloxycarbonyl-2-deoxyfortimicin A (22)

A solution of 3.619 g of 2-azido-1,2′,6′,2″-tetra-N-benzyloxycarbonyl-2-deoxyfortimicin A in 250 ml of methanol is treated for 17 hours with 3.6 g of 5% platinum on carbon under hydrogen and 3 atmospheres of pressure. The catalyst is filtered off and washed with ethanol. The filtrate is concentrated to dryness under reduced pressure to leave 2.60 g of residue. The residue is chromatographed on a column of silica gel using a solvent system consisting of dichloroethane-95% ethanol-concentrated ammonium hydroxide (18:2.0:0.04 v/v) to leave 1.345 g of 2-amino-1,2′,6′,2″-tetra-N-benzyloxycarbonyl-2-deoxyfortimicin A: $[\alpha]_D^{24}+52°$ (c 1.02, methanol); IR (CDCl$_3$) 3415, 1710, 1635 and 1495 cm$^{-1}$; NMR (CDCl$_3$) $\delta$1.15 (d, C$_6'$—CH$_3$, J$_{6',7'}$=6.0 Hz), 2.84 (s, C$_4$—NCH$_3$), 3.26 (s, C$_3$—OCH$_3$), 7.29 (m, Cbz-aromatic).

Anal. Calcd. for C$_{44}$H$_{60}$N$_6$O$_{13}$: C, 62.54; H, 6.43; N, 8.93. Found: C, 62.20; H, 6.53; N, 8.68.

EXAMPLE 27

2-Azido-1,2′,6′,2″-tetra-N-benzyloxycarbonyl-2-deoxyfortimicin A (18)

To a stirred solution of 3.0 g of 1,2′,6′,2″-tetra-N-benzyloxycarbonyl-2-O-methanesulfonylfortimicin A in 167 ml of dimethylformamide heated to 93° in an oil bath, is added 3.0 g of finely divided sodium azide. Stirring is continued at 93° for 18 hours. After cooling to room temperature the reaction mixture is poured into 1665 ml of water and extracted in series with three 555 ml portions of chloroform. The chloroform extract is washed in series with three 555 ml portions of water and dried over anhydrous magnesium sulfate. The chloroform is evaporated under reduced pressure and the dimethylformamide is removed by repeated codistillation with toluene. The residue is chromatographed on silica gel. Elution with a solvent system composed of benzene-methanol-95% ethanol-concentrated ammonium hydroxide (23.5:1.4:2.0:0.2 v/v) gives 1.712 g of 2-azido-1,2′,6′,2″-tetra-N-benzyloxycarbonyl-2-deoxyfortimicin A: $[\alpha]_D^{\cong}+34°$ (c 1.05, methanol); IR (CDCl$_3$) $\delta$1.17 (d, C$_6'$—CH$_3$, J$_{6',7'}$=6.0 Hz), 2.78 (s, C$_4$—NCH$_3$), 3.34 (s, C$_3$—OCH$_3$), 7.34 (m, Cbz-aromatic).

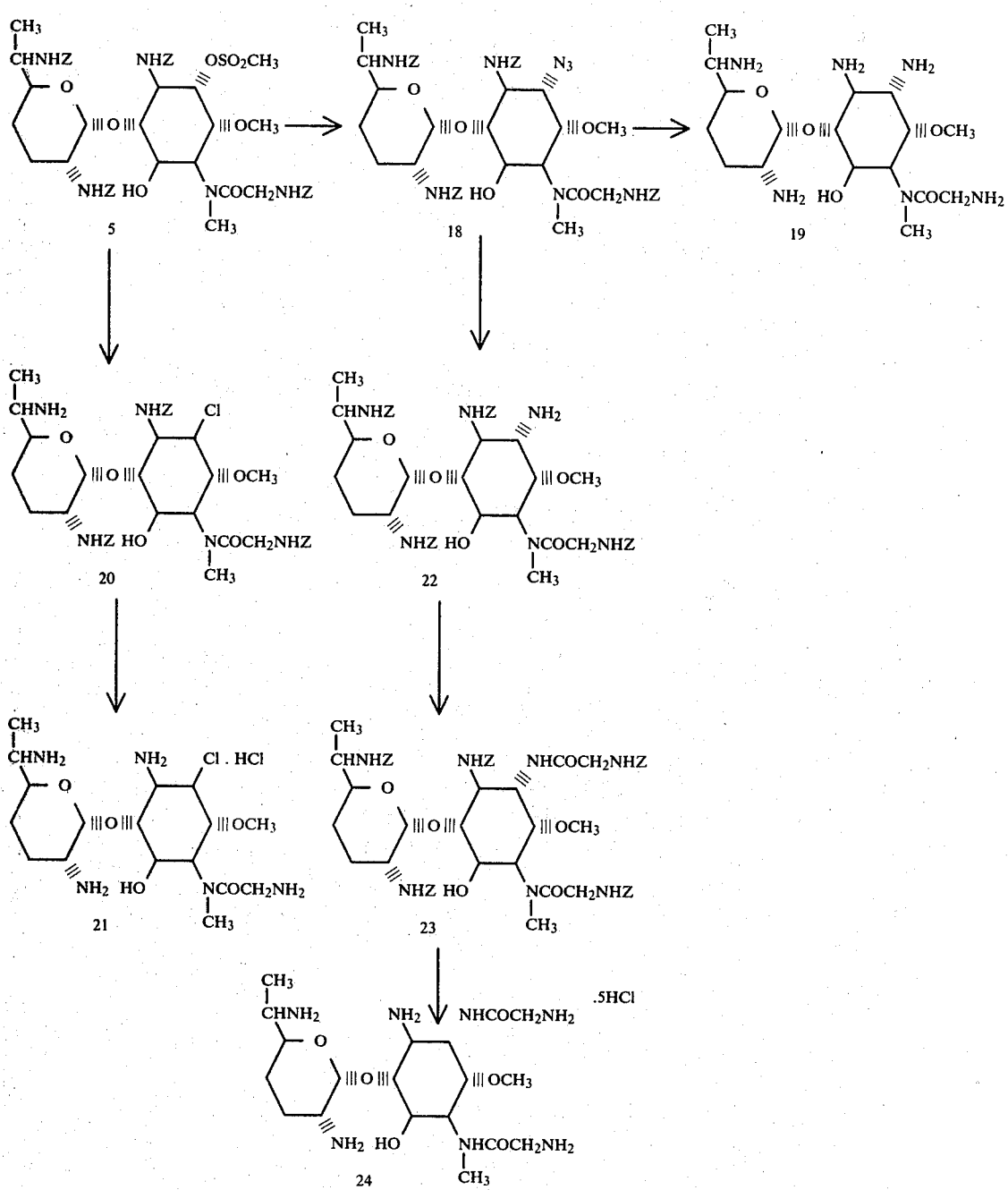

Anal. Calcd. for $C_{44}H_{58}N_8O_{13}$: C, 60.86; H, 6.05; N, 11.59. Found: C, 60.55; H, 6.21; N, 11.49.

EXAMPLE 28

1,2′,6′,2″-Tetra-N-benzyloxycarbonylfortimicin A (27)

Crude fortimicin A sulfate (12.0 g, 17 mmol) is dissolved in distilled water (40 ml) and treated with triethylamine (8.1 g, 80 mmol), followed by acetonitrile (200 ml). With good agitation, N-benzyloxycarbonyloxysuccinimide (25 g, 100 mmol) is added and the mixture is stirred for 6 hours. Removal of solvent in vacuo affords a syrup which is dissolved in methylene chloride (150 ml) and treated with 5% aqueous sodium carbonate (2–50 ml portions) and water (50 ml), then dried over magnesium sulfate. Filtration and removal of solvent provides a clear foam which is chromatographed over silica gel using a stepwise ethylene dichloride:ethanol gradient (100/0 to 95/5). Concentration of appropriate fractions affords pure 1,2′,6′,2″tetra-N-benzyloxycarbonylfortimicin A (15.3 g, 16.2 mmol. 95.5%): IR (CDCl$_3$) 3460–3250, 2940, 1705, 1630, 1500, 1220, 1040, and 1015 cm$^{-1}$; NMR (C$_5$D$_5$N, 100°) 1.12 (d, J=6.5 Hz, C$_{6'}$—CH$_3$), 1.30–2.02 (m, C$_{3'}$H$_2$—C$_{4'}$H$_2$), 2.99 (s, N—CH$_3$), 3.16 (s, OCH$_3$), 4.98–5.10 (m, benzyl CH$_2$), and 7.04–7.33 (m, aromatic CH); CMR (CD$_3$SOCD$_3$, 100°) 17.36, 23.81, 26.67, 30.99, 42.74, 49.81, 50.17, 52.86, 55.59, 65.31–65.78 (4 carbons), 68.45, 70.44, 71.72, 73.37, 76.47, 96.63, 127.44–128.20 (several carbons), 136.97–137.43 (4 carbons), 155.14–156.03 (4 carbons), and 169.35 ppm.

Anal. Calcd. for $C_{49}H_{59}N_5O_{14}$: C, 62.48; H, 6.31; N, 7.43. Found: C 62.30; H, 6.34; N, 7.48.

EXAMPLE 29

1,2',6',2''-Tetra-N-benzyloxycarbonyl-2-O-methanesulfonylfortimicin A (5)

A solution of 1,2',6',2''-tetra-N-benzyloxycarbonyl-fortimicin A (7.0 g, 7.7 mmol) in dry pyridine (60 ml) is cooled to 0°-5° C. and methanesulfonyl chloride (1.41 g, 12.3 mmol) is introduced dropwise over 7 minutes. After stirring at 0°-5° for 5 hours, the reaction mixture is treated with a second portion of methanesulfonyl chloride (160 mg, 1.4 mmol) and stirred for an additional 2 hours. The mixture is quenched with a chip of ice and solvent is removed in vacuo to provide a syrup, which is taken up into methylene chloride (80 ml) and washed successively with 5% aqueous hydrochloric acid (2-20 ml portions), 5% aqueous sodium bicarbonate (2-20 ml portions) and water (20 ml). The organic layer is dried over magnesium sulfate, filtered and concentrated to give the 2-O-methanesulfonate, contaminated with 10-15% of 1,2',6',2''-tetra-N-benzyloxycarbonyl-2,5-O-dimethanesulfonylfortimicin A. The crude methanesulfonate is purified by column chromatography over silica gel using toluene-isopropanol (98/2 to 97/3). Pure 1,2',6',2''-tetra-N-benzyloxycarbonyl-2-O-methanesulfonylfortimicin A has IR (CDCl$_3$) 3475-3300, 2952, 1717, 1640, 1502, 1365, 1222, 1175 and 1042 cm$^{-1}$; NMR (C$_5$D$_5$N, 110°) δ1.27 (d, J=6.6 Hz, C$_6'$—CH$_3$), 1.40-2.20 (m, C$_3'$H$_2$—C$_4'$H$_2$), 3.13 (s, N—CH$_3$), 3.18 (s, O$_2$S—CH$_3$), 3.40 (s, OCH$_3$), 5.12-5.26 (m, benzyl CH$_2$), and 7.16-7.48 (m, aromatic CH); CMR (CD$_3$SOCD$_3$, 100°) 17.36, 23.62, 26.71, 31.51, 37.53, 38.35, 42.73, 49.80, 50.15, 52.84, 53.66, 56.87, 65.36-66.17 (4 carbons), 70.56, 71.19, 72.01, 75.57, 77.61, 96.57, 126.9-128.78 (several carbons), 136.67-137.41 (4 carbons), 155.08-156.01 (4 carbons) and 169.52 ppm.

Anal. Calcd. for $C_{50}H_{61}N_5O_{16}S$: C, 58.87; H, 6.03; N, 6.86; S, 3.14. Found: C, 58.85; H, 6.19; N, 6.86; S, 2.85.

EXAMPLE 30

2-Azido-1,2',6',2''-tetra-N-benzyloxycarbonyl-2-deoxyfortimicin A (18)

1,2',6',2''-Tetra-N-benzyloxycarbonyl-2-O-methanesulfonylfortimicin A (5.0 g, 4.9 mmol) is dissolved in dimethylformamide (250 ml) and heated to 93°. Sodium azide (5.0 g, 76.9 mmol) is added with good agitation and the reaction mixture is stirred at 93° for 4 hours. After cooling to 25°, the suspension is treated with ether (250 ml) to precipitate excess sodium azide. Filtration, followed by concentration of the filtrate in vacuo, affords a semi-solid mass which is taken up into methylene chloride (80 ml), washed with 3-20 ml portions of water, then dried over magnesium sulfate. Filtration and concentration under reduced pressure gives a partially solidified syrup which is chromatographed over silica gel using a stepwise gradient of toluene-isopropanol (98-2 97-3). Concentration of appropriate fractions affords 2.96 g (3.06 mmol, 62%) of pure 2-azido-1,2',6',2''-tetra-N-benzyloxycarbonyl-2-deoxyfortimicin A: IR (CDCl$_3$) 3480-3170, 2955, 2112, 1715, 1640, 1502, 1222 and 1040 cm$^{-1}$; NMR (C$_5$D$_5$N, 110°) δ1.27 (d, J=7 Hz, C$_6'$—CH$_3$), 1.40-2.20 (m, C$_3'$H$_2$—C$_4'$H$_2$), 3.12 (s, N—CH$_3$), 3.35 (s, OCH$_3$), 5.18-5.30 (m, benzyl CH$_2$) and 7.18-7.48 (m, aromatic C—H); CMR (CD$_3$SOCD$_3$, 100°) 17.20, 23.69, 26.48, 31.70, 42.79, 49.75, 50.27, 53.03, 53.67, 56.61, 60.58, 65.36-66.00 (4 carbons), 70.51, 71.16, 74.13, 76.41, 96.57, 127.45-128.78 (several carbons), 136.80-137.37 (4 carbons), 155.15-156.02 (4 carbons) and 169.52 ppm.

Anal. Calcd. for $C_{49}H_{58}N_8O_{13}$: C, 60.86; H, 6.05; N, 11.59. Found: C, 61.14; H, 6.32; N, 11.62.

EXAMPLE 31

2-Amino-2-deoxyfortimicin A Sulfate

A solution of 2.54 g (2.63 mmol) of 2-azido-1,2',6',2''-tetra-N-benzyloxycarbonyl-2-deoxyfortimicin A in 263 ml of 0.2 N methanolic hydrogen chloride is treated with hydrogen (3 atm.) over 2.54 g of 5% palladium on carbon for 5 hours. The catalyst is removed by filtration and washed with methanol. The filtrate is concentrated to dryness and the residual hydrochloric acid is removed by repeated distillation in vacuo with methanol to provide 1.6 g of 2-amino-2-deoxyfortimicin A pentahydrochloride as a hydrate. Passage of an aqueous solution of the hydrochloride over a column of AG 1×2 (sulfate) ion exchange resin converts it to the sulfate form. 2-Amino-2-deoxyfortimicin A sulfate has IR (KBr) 3660-3330, 2950, 2650, 1635, 1524 and 1120-960 cm$^{-1}$; NMR (D$_2$O) 1.47 (d, J=6.5 Hz) (C$_6'$—CH$_3$), 1.56-2.31 (m, C$_3'$H$_2$—C$_4'$H$_2$), 3.27 (s, NCH$_3$), 3.68 (s, OCH$_3$), and 5.48 (d, J=3 Hz, C$_1'$—H); CMR (D$_2$O) 14.85; 21.45, 26.26, 31.74, 41.33, 49.35 (2 carbons), 51.26 (2 carbons), 51.85, 58.28, 69.97, 70.80, 71.14, 73.55, 96.27 and 168.94 ppm; mass spectrum, free base, (m/e) 404 (M+.), 245, 143; [ ]+69° (c 1.02 water).

Anal. Calcd. for $C_{17}H_{36}N_6O_5.5/2\ H_2SO_4.3/2\ H_2O$: C, 30.17; H, 6.55; N, 12.42; S, 11.85. Found: C, 29.97; H, 6.45; N, 12.33; S. 11.44.

The in vitro antibiotic activity of the compounds of this invention are determined by a two-fold agar dilution method using 10 ml of Mueller-Hinton agar per Petri dish. The agar is inoculated with one loopful (0.001 ml loop) of a 1:10 dilution of a 24 hour broth culture of the indicated test organism and incubated at 37° for 24 hours. The activities are listed in the following Table. Minimum inhibitory concentration (MIC) is expressed in mcg/ml.

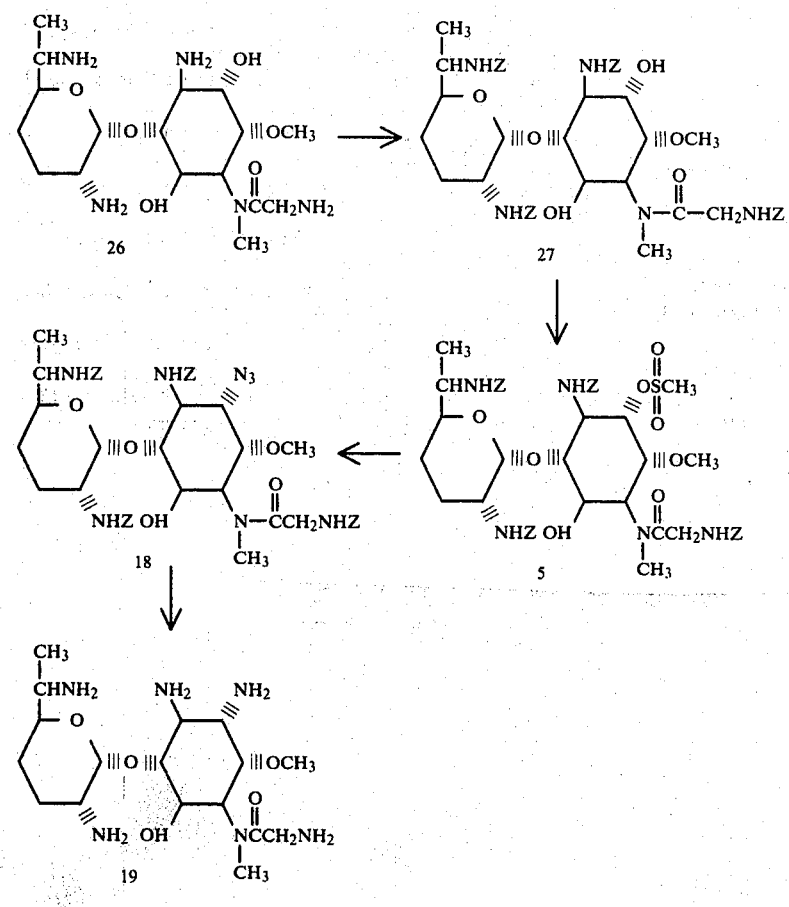

TABLE

| | In Vitro Antibiotic Activity of Compounds of the Invention | | | | | | | | |
|---|---|---|---|---|---|---|---|---|---|
| Organism | Fort. A SO$_4$ Control | Fort. A HCl Control | 6 | 7 | 8 | 25 | 19 | 24 | 2 |
| *Staph. aureus* Smith | 0.78 | 1.56 | 25 | 25 | 12.5 | 3.1 | 1.56 | 3.1 | 1.56 |
| *Strep. faecalis* 10541 | 50 | 50 | >100 | >100 | >100 | 100 | 100 | >100 | 50 |
| *Enterobacter aerogenes* 13048 | 3.1 | 6.2 | >100 | >100 | 100 | 25 | 6.2 | 12.5 | 12.5 |
| *E. coli* Juhl | 6.75 | 6.2 | 100 | 100 | 100 | 25 | 12.5 | 50 | 25 |
| *E. coli* BL 3676 (Res) | 25 | 25 | >100 | >100 | >100 | 50 | 50 | 100 | 25 |
| *Kleb. pneumoniae* 10031 | 1.56 | 3.1 | >100 | >100 | 100 | 50 | 3.1 | 6.2 | 50 |
| *Kleb. pneumoniae* KY 4262 | 6.2 | 6.2 | >100 | >100 | >100 | 100 | 12.5 | 25 | 50 |
| *Providencia* 1577 | 1.56 | 3.1 | >100 | >100 | 100 | 50 | 6.2 | 25 | 25 |
| *Pseudo. aeruginosa* BMH #10 | 0.78 | 1.56 | 25 | 25 | 12.5 | 3.1 | 1.56 | 3.1 | 1.56 |
| *Pseudo. aeruginosa* KY 8512 | 12.5 | 25 | >100 | >100 | >100 | 100 | 50 | 100 | 100 |
| *Pseudo. aeruginosa* KY 8516 | 50 | 100 | >100 | >100 | >100 | >100 | 100 | >100 | >100 |
| *Pseudo. aeruginosa* 209 | >100 | >100 | >100 | >100 | >100 | >100 | >100 | >100 | >100 |
| *Pseudo. aeruginosa* 27853 | 12.5 | 12.5 | >100 | >100 | >100 | 100 | 50 | 50 | >100 |
| *Sal. typhimurium* Ed. #9 | 1.56 | 3.1 | 100 | 100 | 50 | 6.2 | 6.2 | 25 | 12.5 |
| *Serratia marcescens* 4003 | 1.56 | 3.1 | >100 | >100 | 50 | 12.5 | 3.1 | 12.5 | 6.2 |
| *Shigella sonnei* 9290 | 12.5 | 12.5 | 100 | 100 | 100 | 25 | 12.5 | 25 | 12.5 |
| *Proteus rettgeri* U6333 | 12.5 | 25 | >100 | >100 | >100 | >100 | 25 | >100 | 50 |
| *Proteus vulgaris* JJ | 6.2 | 6.2 | 100 | 100 | 100 | 25 | 6.2 | 25 | 25 |
| *Proteus mirabilis* Fin #9 | 6.2 | 12.5 | 100 | 50 | >100 | 25 | 12.5 | 50 | 50 |

What is claimed is:

1. A compound of the formula

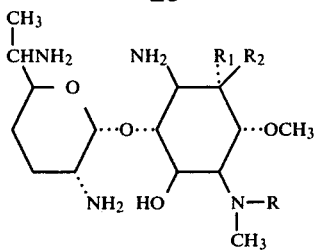

wherein R is hydrogen, glycyl, β-alanyl, acetyl, or β-aminolower-alkyl; $R_1$ is hydrogen, amino, azido, halo, glycylamido, β-alanylamido or 2-O-methanesulfonyl; and $R_2$ is hydrogen or halo, with the proviso that $R_1$ and $R_2$ cannot both be hydrogen; and their pharmaceutically acceptable salts.

2. A compound of claim 1 wherein R is hydrogen or glycyl, $R_1$ is hydrogen, amino, azido, chloro, glycylamido or 2-O-methansulfonyl and $R_2$ is hydrogen or chloro.

3. The compound of claim 2 wherein R is glycyl, $R_1$ is glycylamido and $R_2$ is hydrogen.

4. The compound of claim 2 wherein R is glycyl, $R_1$ is amino and $R_2$ is hydrogen.

5. The compound of claim 2 wherein R is glycyl, $R_1$ is hydrogen and $R_2$ is chloro.

6. The compound of claim 2 wherein R is glycyl, $R_1$ is azido and $R_2$ is hydrogen.

7. The compound of claim 2 wherein R is hydrogen, $R_1$ is azido and $R_2$ is hydrogen.

8. The compound of claim 2 wherein R is glycyl, $R_1$ is chloro and $R_2$ is hydrogen.

9. The compound of claim 2 wherein R is hydrogen, $R_1$ is chloro and $R_2$ is hydrogen.

10. The compound of claim 2 wherein R is glycyl, $R_1$ is 2-O-methanesulfonyl and $R_2$ is hydrogen.

* * * * *